United States Patent
Gambale et al.

(10) Patent No.: US 6,432,126 B1
(45) Date of Patent: Aug. 13, 2002

(54) FLEXIBLE VASCULAR INDUCING IMPLANTS

(75) Inventors: Richard A. Gambale, Tyngsboro; Stephen J. Forcucci, Arlington; Michael F. Weiser, Groton; Richard T. Choh, Lowell; Sean Forde, Watertown, all of MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/164,163

(22) Filed: Sep. 30, 1998

(51) Int. Cl.$^7$ .................................................. A61F 2/06
(52) U.S. Cl. ........................................................ 623/1.1
(58) Field of Search ............................. 623/1.42, 1.43, 623/139, 23.64, 8, 14

(56) References Cited

U.S. PATENT DOCUMENTS

| | | |
|---|---|---|
| 3,991,750 A | 11/1976 | Vickery |
| 3,995,617 A | 12/1976 | Watkins et al. |
| 4,307,722 A | 12/1981 | Evans et al. |
| 4,503,569 A | 3/1985 | Dotter |
| 4,546,499 A | 10/1985 | Possis |
| 4,562,597 A | 1/1986 | Possis et al. |
| 4,580,568 A | 4/1986 | Gianturco |
| 4,582,181 A | 4/1986 | Samson |
| 4,641,653 A | 2/1987 | Rockey |
| 4,649,922 A | 3/1987 | Wiktor |
| 4,655,771 A | 4/1987 | Wallsten |
| 4,658,817 A | 4/1987 | Hardy et al. |
| 4,665,918 A | 5/1987 | Garza et al. |
| 4,681,110 A | 7/1987 | Wiktor |
| 4,733,665 A | 3/1988 | Palmaz |
| 4,768,507 A | 9/1988 | Fischell et al. |
| 4,774,949 A | 10/1988 | Fogarty |
| 4,813,925 A | 3/1989 | Anderson, Jr. et al. |
| 4,861,330 A | 8/1989 | Voss |
| 4,889,137 A | 12/1989 | Kolobow |

(List continued on next page.)

FOREIGN PATENT DOCUMENTS

| | | |
|---|---|---|
| DE | 19703482 | 1/1997 |
| DE | 296 19 029 u1 | 4/1997 |
| EP | 0 490 459 A1 | 6/1992 |
| EP | 0 515 867 A2 | 12/1992 |
| EP | 0 714 640 A1 | 6/1996 |
| EP | 0 717 969 A2 | 6/1996 |
| EP | 0 732 089 A2 | 9/1996 |
| EP | 0 812 574 A2 | 12/1997 |
| EP | 0 830 873 A2 | 3/1998 |
| EP | 0 853 931 A2 | 7/1998 |

(List continued on next page.)

OTHER PUBLICATIONS

Neil B. Ingels, et al., Measurement of Midwall Myocardial Dynamics in Intact Man by Radiography of Surgically Implanted Markers, Circulation, vol. 52, pp. 859–867 (Nov. 1975).

A. Hassan Khazei et al., Myocardial Canalization, A New Method of Myocardial Revascularization, The Annals of Thoracic Surgery, vol. 6, No. 2, pp. 163–171, Aug. 1968.

(List continued on next page.)

*Primary Examiner*—Gene Mancene
*Assistant Examiner*—Eduardo C. Robert
(74) *Attorney, Agent, or Firm*—Kirkpatrick & Lockhart LLP

(57) ABSTRACT

Implants and associated delivery systems for promoting angiogenesis in ischemic tissue are provided. The implants may be delivered percutaneously, thoracically or surgically and are particularly well suited for implantation into the myocardium of the heart. The implants are configured to be flexible so that they compress and expand with corresponding movement of the surrounding tissue into which they are implanted. The flow of blood into the implant and pooling of the blood in and around the implant leads to thrombosis and fibrin growth, a healing process that leads to angiogenesis in the tissue surrounding the implant. Additionally, the implants may contain an angiogenic substance or a thrombus of blood, preloaded or injected after implantation to aid in initiating angiogenesis.

28 Claims, 7 Drawing Sheets

U.S. PATENT DOCUMENTS

| | | |
|---|---|---|
| 4,904,264 A | 2/1990 | Scheunemann |
| 4,917,666 A | 4/1990 | Solar |
| 4,920,980 A | 5/1990 | Jackowski |
| 4,950,227 A | 8/1990 | Savin et al. |
| 4,995,857 A | 2/1991 | Arnold |
| 4,997,431 A | 3/1991 | Isner et al. |
| 5,040,543 A | 8/1991 | Badera et al. |
| 5,042,486 A | 8/1991 | Pfeiler et al. |
| 5,047,028 A | 9/1991 | Qian |
| 5,049,138 A | 9/1991 | Chevalier et al. |
| 5,056,517 A | 10/1991 | Fenici |
| 5,087,243 A | 2/1992 | Avitall |
| 5,098,374 A | 3/1992 | Othel-Jacobsen et al. |
| 5,114,414 A | 5/1992 | Buchbinder |
| 5,158,548 A | 10/1992 | Lau et al. |
| 5,167,614 A | 12/1992 | Tessman et al. |
| 5,176,626 A | 1/1993 | Soehendra |
| 5,180,366 A | 1/1993 | Woods |
| 5,190,058 A | 3/1993 | Jones et al. |
| 5,256,146 A | 10/1993 | Ensminger et al. |
| 5,266,073 A | 11/1993 | Wall |
| 5,287,861 A | 2/1994 | Wilk |
| 5,290,678 A | 3/1994 | Jackowski |
| 5,312,456 A | 5/1994 | Reed et al. |
| 5,314,471 A * | 5/1994 | Brauker et al. ............... 623/11 |
| 5,324,325 A | 6/1994 | Moaddeb |
| 5,366,493 A | 11/1994 | Scheiner et al. |
| 5,372,600 A | 12/1994 | Beyar et al. |
| 5,380,316 A | 1/1995 | Alta et al. |
| 5,383,929 A * | 1/1995 | Ledergerber ................. 623/11 |
| 5,389,096 A | 2/1995 | Alta et al. |
| 5,391,199 A | 2/1995 | Ben-Haim |
| 5,409,004 A | 4/1995 | Sloan |
| 5,409,019 A | 4/1995 | Wilk |
| 5,423,885 A | 6/1995 | Williams |
| 5,425,757 A | 6/1995 | Tiefenbrun et al. |
| 5,429,144 A | 7/1995 | Wilk |
| 5,441,516 A | 8/1995 | Wang et al. |
| 5,452,733 A | 9/1995 | Sterman |
| 5,453,090 A | 9/1995 | Martinez et al. |
| 5,458,615 A | 10/1995 | Klemm |
| 5,464,404 A | 11/1995 | Abela et al. |
| 5,464,650 A | 11/1995 | Berg et al. |
| 5,466,242 A | 11/1995 | Mori |
| 5,476,505 A | 12/1995 | Limon |
| 5,480,422 A | 1/1996 | Ben-Halm |
| 5,487,739 A | 1/1996 | Aebischer et al. |
| 5,514,176 A | 5/1996 | Bosley, Jr. et al. |
| 5,551,427 A | 9/1996 | Altman |
| 5,551,954 A | 9/1996 | Buscemi et al. |
| 5,562,619 A | 10/1996 | Mirarchi et al. |
| 5,562,922 A | 10/1996 | Lambert |
| 5,569,272 A | 10/1996 | Reed et al. |
| 5,571,168 A | 11/1996 | Toro |
| 5,593,412 A | 1/1997 | Martinez et al. |
| 5,593,434 A | 1/1997 | Williams |
| 5,602,301 A | 2/1997 | Field |
| 5,614,206 A | 3/1997 | Randolph et al. |
| 5,643,308 A | 7/1997 | Markman |
| 5,653,756 A | 8/1997 | Clarke et al. |
| 5,655,548 A | 8/1997 | Nelson |
| 5,662,124 A | 9/1997 | Wilk |
| 5,676,850 A | 10/1997 | Reed |
| 5,690,643 A | 11/1997 | Wijay |
| 5,735,897 A | 4/1998 | Buirge |
| 5,741,330 A | 4/1998 | Brauker et al. |
| 5,744,515 A | 4/1998 | Clapper |
| 5,755,682 A | 5/1998 | Knudson et al. |
| 5,756,127 A | 5/1998 | Grisoni et al. |
| 5,762,600 A | 6/1998 | Bruchman et al. |
| 5,769,843 A | 6/1998 | Abela et al. |
| 5,782,823 A | 7/1998 | Mueller |
| 5,785,702 A | 7/1998 | Murphy et al. |
| 5,792,453 A | 8/1998 | Hammond et al. |
| 5,797,870 A | 8/1998 | March et al. |
| 5,807,384 A | 9/1998 | Mueller |
| 5,810,836 A | 9/1998 | Hussein |
| 5,824,049 A | 10/1998 | Ragheb et al. |
| 5,824,071 A | 10/1998 | Nelson et al. |
| 5,830,502 A | 11/1998 | Dong et al. |
| 5,840,059 A | 11/1998 | March et al. |
| 5,843,069 A * | 12/1998 | Butler et al. ............. 604/891.1 |
| 5,861,032 A | 1/1999 | Subramaniam |
| 5,879,383 A | 3/1999 | Bruchman et al. |
| 5,899,915 A | 5/1999 | Saadat |
| 5,971,993 A | 10/1999 | Hussein et al. |
| 5,980,514 A | 11/1999 | Kupiecki et al. |
| 6,045,565 A | 4/2000 | Ellis et al. |
| 6,053,924 A | 4/2000 | Hussein |

FOREIGN PATENT DOCUMENTS

| | | |
|---|---|---|
| EP | 0 953 320 A2 | 11/1999 |
| FR | 1514319 | 1/1967 |
| FR | 2 725 615 | 10/1994 |
| RU | 2026640 C1 | 1/1995 |
| RU | 2063179 C1 | 7/1996 |
| WO | WO 89/01798 | 3/1989 |
| WO | WO 91/15254 | 10/1991 |
| WO | WO 94/05265 | 3/1994 |
| WO | WO 94/27612 | 12/1994 |
| WO | WO 95/33511 | 12/1995 |
| WO | WO 96/20698 | 7/1996 |
| WO | WO 97/42910 | 7/1997 |
| WO | WO 97/32551 | 9/1997 |
| WO | WO 97/38730 | 10/1997 |
| WO | WO 97/44071 | 11/1997 |
| WO | WO 97/45105 | 12/1997 |
| WO | WO 97/47253 | 12/1997 |
| WO | WO 98/05307 | 2/1998 |
| WO | WO 98/08456 | 3/1998 |
| WO | WO 98/16644 | 4/1998 |
| WO | WO 98/23228 | 6/1998 |
| WO | WO 98/25533 | 6/1998 |
| WO | WO 98/29148 | 7/1998 |
| WO | WO 98/32859 | 7/1998 |
| WO | WO 98/46115 | 10/1998 |
| WO | WO 99/21510 | 5/1999 |
| WO | WO 99/38459 | 8/1999 |
| WO | WO 99/53863 | 10/1999 |

OTHER PUBLICATIONS

Alfred Goldman et al., Experimental Methods for Producing a Collateral Circulation to the Heart Directly from the Left Ventricle, Journals of Thoracic Surgery, vol. 31, No. 3, pp. 364–374. Mar. 1956.

A. Sachinopoulou et al., Invited Review Transmyocardial Revascularization, Lasers in Medical Science 1995, vol. 10, pp.83–91, Sep. 1995.

B. Schumacher, Induction of Neoangiogenesis in Ischemic Myocardium by Human Growth Factors, First Clinical Results of a New Treatment of Coronary Heart Disease, Clinical Investigation and Reports, pp 645–650, Dec. 1997.

Charles T. Doiter, Transluminally–placed Coilspring Endarterial Tube Grafts, Long–term Patency in Canine Popliteral Artery, Investigative Radiology, pp. 329–332, Sep.–Oct. 1969.

C. Massimo, et al., Myocardial Revascularization By a New Method of Carrying Blood Directly from the Left Ventricular Cavity into the Coronary Circulation, Journals of Thoracic Surgery, vol. 34, No. 2, pp. 257–264, Aug. 1957.

Garrett Lee et al., Feasibility of Intravascular Laser Irradiation for in Vivo Visualization and Therapy of Cardiocirculatory Diseases, American Heart Journal, vol. 103 No. 6, pp. 1076–1077.

Garrett Lee et al., Laser–Dissolution of Coronary Atherosclerotic Obstruction, American Heart Journal, vol. 102, No. 6, part 1, pp. 1074–1075. Dec. 1981.

George S. Abela et al., Use of Laser Radiation to Recanalize Totally Obstructed Coronary Arteries (Abstract), Journal American College Cardiology 1983:1(2):691.

George S. Abela et al., Laser Revascularization: What Are Its Prospects?, Journal of Cardiovascular Medicine, pp. 977–984, Sep. 1983.

Isam N. Anabtawi et al., Experimental Evaluation of Myocardial Tunnelization as a Method of Myocardial Revascularization, Journal of Thoracic and Cardiovascular Surgery, vol. 58, No. 5, pp. 638–646, Nov. 1969.

John E. Hersey et al., Transmyocardial Puncture Revascularization, Geriatrics, pp. 101–108, Mar. 1969.

Ladislav Kuzela et al., Experimental Evaluation of Direct Transventricular Revascularization, Journal of Thoracic Cardiovascular Surgery, vol. 57, No. 6, pp. 770–773, Jun. 1969.

Mahmood Mihoseini et al., Myocardial Revascularization by Laser: A Clinical Report; Lasers in Surgery and Medicine 3: 241–245 (1983).

Mahmood Mirhoseini et al., Revascularization of the Heart by Laser; Journal of Microsurgery, pp. 253–260, Jun. 1981.

Mahmood Mirhoseini et al., Transventricular Revascularization by Laser, Lasers in Surgery and Medicine, vol. 2, pp. 187–198, 1982.

Mahmood Mirhoseini et al., Clinical Report: Laser Myocardial Revascularization, Lasers in Surgery and Medicine vol. 6, pp. 459–461, 1986.

Mahmood Mirhoseini et al., New Concepts in Revascularization of the Myocardium, The Annals of Thoracic Surgery, vol. 45, No. 4, pp. 415–420, Apr. 1988.

P. Walter et al., Treatment of Acute Myocardial Infarction by Transmural Blood Supply from the Ventricular Cavity, Department of Surgery and Department of Radiology of the Hannover Medical School, Hanover, pp 130–138, (1971).

Peter Whittaker, et al., Transmural Channels Can Protect Ischemic Tissue, Assessment of Long–term Myocardial Response to Laser and Needle–Made Channels Circulation, vol. 93, No. 1, pp. 143–152, Jan. 1996.

P.K. Sen, et al, Further Studies in Multiple Transmyocardial Acupuncture as a Method of Myocardial Revascularization, Surgery, vol. 64, No. 5, pp. 861–870, Nov. 1968.

P.K. Sen et al, Transmyocardial Acupuncture, A New Approach to Myocardial Revascularization; Journal of Thorocic and Cardiovascular Surgery, vol. 50, No. 2, pp. 181–189, Aug. 1965.

R.I. Hardy et al., Regional Myocardial Blood Flow and Cardiac Mechanics in Dog Hearts with $CO_2$Laser–Induced Intramyocardial Revascularization, Basic Research Cardiology, 85:179–197 (199).

Roque Pifarre et al., Myocardial Revascularization by Transmyocardial Acupuncture: A Physiologic Impossibility; Journal of Thoracic and Cardiovascular Surgery; vol. 58, No. 3, pp. 424–429, Sep. 1969.

Valluvan Jeevanandam et l., Myocardial Revascularization by Laer–Induced Channels, Surgical Forum vo. IVL, American College of Surgeons 76th Clinical Congress, vol. 4, pp. 225–227, Oct. 1990.

* cited by examiner

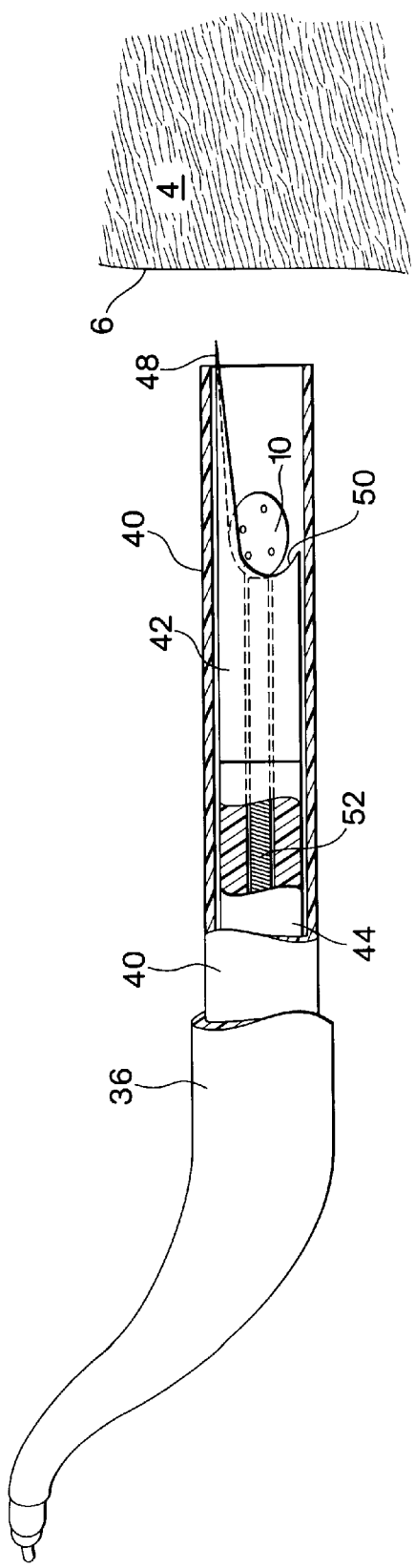
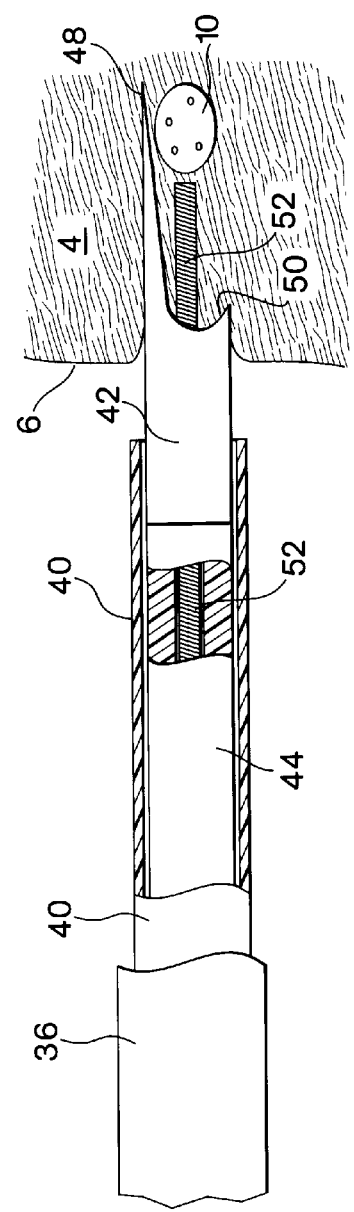
Fig. 3A
Fig. 3B

FLEXIBLE VASCULAR INDUCING IMPLANTS

FIELD OF THE INVENTION

This invention relates to methods and devices for inducing angiogenesis in ischemic tissue.

BACKGROUND OF THE INVENTION

Tissue becomes ischemic when it is deprived of adequate blood flow. Ischemia causes pain in the area of the affected tissue and, in the case of muscle tissue, can interrupt muscular function. Left untreated, ischemic tissue can become infarcted and permanently non-functioning. Ischemia can be caused by a blockage in the vascular system that prohibits oxygenated blood from reaching the affected tissue area. However, ischemic tissue can be revived to function normally despite the deprivation of oxygenated blood because ischemic tissue can remain in a hibernating state, preserving its viability for some time. Restoring blood flow to the ischemic region serves to revive the ischemic tissue.

Although ischemia can occur in various regions of the body, often tissue of the heart, the myocardium, is affected by ischemia due to coronary artery disease, occlusion of the coronary artery, which otherwise provides blood to the myocardium. Muscle tissue affected by ischemia can cause pain to the individual affected. Ischemia can be treated, if a tissue has remained viable despite the deprivation of oxygenated blood, by restoring blood flow to the affected tissue.

Treatment of myocardial ischemia has been addressed by several techniques designed to restore blood supply to the affected region. Coronary artery bypass grafting CABG involves grafting a venous segment between the aorta and the coronary artery to bypass the occluded portion of the artery. Once blood flow is redirected to the portion of the coronary artery beyond the occlusion, the supply of oxygenated blood is restored to the area of ischemic tissue.

Early researchers, more than thirty years ago, reported promising results for revascularizing the myocardium by piercing the muscle to create multiple channels for blood flow. Sen, P. K. et al., "Transmyocardial Acupuncture—A New Approach to Myocardial Revascularization", *Journal of Thoracic and Cardiovascular Surgery*, Vol. 50, No. 2, August 1965, pp. 181–189. Although others have reported varying degrees of success with various methods of piercing the myocardium to restore blood flow to the muscle, many have faced common problems such as closure of the created channels. Various techniques of perforating the muscle tissue to avoid closure have been reported by researchers. These techniques include piercing with a solid sharp tip wire, hypodermic tube and physically stretching the channel after its formation. Reportedly, many of these methods still produced trauma and tearing of the tissue that ultimately led to closure of the channel.

An alternative method of creating channels that potentially avoids the problem of closure involves the use of laser technology. Researchers have reported success in maintaining patent channels in the myocardium by forming the channels with the heat energy of a laser. Mirhoseini, M. et al., "Revascularization of the Heart by Laser", *Journal of Microsurgery*, Vol. 2, No. 4, June 1981, pp. 253–260. The laser was said to form channels in the tissue were clean and made without tearing and trauma, suggesting that scarring does not occur and the channels are less likely to experience the closure that results from healing. U.S. Pat. No. 5,769,843 (Abela et al.) dicloses creating laser-made TMR channels utilizing a catheter based system. Abela also discloses a magnetic navigation system to guide the catheter to the desired position within the heart. Aita U.S. Pat. Nos. 5,380, 316 and 5,389,096 disclose another approach to a catheter based system for TMR.

Although there has been some published recognition of the desirability of performing transmyocardial revascularization (TMR) in a non-laser catheterization procedure, there does not appear to be evidence that such procedures have been put into practice. For example, U.S. Pat. No. 5,429,144 Wilk discloses inserting an expandable implant within a preformed channel created within the myocardium for the purposes of creating blood flow into the tissue from the left ventricle.

Performing TMR by placing stents in the myocardium is also disclosed in U.S. Pat. No. 5,810,836 (Hussein et al.). The Hussein patent discloses several stent embodiments that are delivered through the epicardium of the heart, into the myocardium and positioned to be open to the left ventricle. The stents are intended to maintain an open channel in the myocardium through which blood enters from the ventricle and perfuses into the myocardium.

Angiogenesis, the growth of new blood vessels in tissue, has been the subject of increased study in recent years. Such blood vessel growth to provide new supplies of oxygenated blood to a region of tissue has the potential to remedy a variety of tissue and muscular ailments, particularly ischemia. Primarily, study has focused on perfecting angiogenic factors such as human growth factors produced from genetic engineering techniques. It has been reported that injection of such a growth factor into myocardial tissue initiates angiogenesis at that site, which is exhibited by a new dense capillary network within the tissue. Schumacher et al., "Induction of Neo-Angiogenesis in Ischemic Myocardium by Human Growth Factors", *Circulation*, 1998; 97:645–650. The authors noted that such treatment could be an approach to management of diffused coronary heart disease after alternative methods of administration have been developed.

SUMMARY OF THE INVENTION

The vascular inducing implants of the present invention provide a mechanism for initiating angiogenesis within ischemic tissue. The implants interact with the surrounding tissue in which they are implanted and the blood that is present in the tissue to initiate angiogenesis by various mechanisms.

Primarily, it is expected that the implants will trigger angiogenesis in the ischemic tissue by interacting in one or more ways with the tissue to initiate an injury response. The body's response to tissue injury involves thrombosis formation at the site of the injury or irritation. Thrombosis leads to arterioles and fibrin growth which is believed to ultimately lead to new blood vessel growth to feed the new tissue with blood. The new blood vessels that develop in this region also serve to supply blood to the surrounding area of ischemic tissue that was previously deprived of oxygenated blood.

The presence of the implants in the tissue, alone, may trigger a foreign body response leading to endothelialization and fibrin growth around the implant. However, the implants of the present invention are specially configured to interact with the surrounding tissue to induce angiogenesis by a variety of mechanisms.

Implant embodiments of the invention serve to initiate angiogenesis by providing a chamber or interior into which blood may enter and collect leading to thrombosis. The implants are configured to have a wall defining an interior, with at least one opening in the wall to permit passage of blood into and from the interior. The material and structure of the implants permits them to be flexible such that the implant compresses when the surrounding tissue contracts and the implant returns to an uncompressed configuration when the surrounding tissue relaxes. Cyclical compression and expansion of the implant in concert with the motion of the surrounding tissue creates a pumping action, drawing blood into the implant interior when expanded, then expelling the blood when the implant is compressed. One of the openings of the implant may include a check valve to control the flow of blood from the implant interior. Blood that enters the interior of the implant and remains, evenly temporarily, tends to coagulate and thrombose. Over time, continued pooling of the blood in the interior will cause thrombosis and fibrin growth throughout the interior of the implant and into the surrounding tissue. New blood vessels will grow to serve the new growth with oxygenated blood, the process of angiogenesis.

Some embodiments are configured to have a high degree of flexibility such that they collapse completely under the compressive force of surrounding tissue in contraction. The highly flexible implants are configured to return to their uncompressed, volume defining shape when the surrounding tissue relaxes. The reduction of the volume defined by the interior to practically zero provides significant volume change providing pronounced pumping action to maximize blood exchange through the interior. Thrombosis can occur naturally in the highly flexible embodiments despite the increased blood flow through the interior. However, the highly flexible embodiments are also well suited to pump out into surrounding tissue substances pre-installed within their interior.

Implant embodiments may further be prepared to initiate angiogenesis by having a thrombus of blood associated with them at the time of their implantation or inserted in the interior immediately following implantation. The thrombus of blood may be taken from the patient prior to the implant procedure and is believed to help initiate the tissue's healing response which leads to angiogenesis.

Alternatively or in addition to a thrombus of blood, the implant devices may be preloaded with an angiogenic substance in a variety of ways to aid the process of angiogenesis in embodiments having a defined chamber or interior, the substance may be placed within the interior prior to implantation or injected after the implantation of the device. The substance may be fluid or solid. The blood flow into and interacting with the interior of the device will serve to distribute the substance through the surrounding tissue area because blood entering the device mixes with and then carries away the substance as it leaves the device. Viscosity of the substance and opening size through which it passes, determine the time-release rate of the substance.

Substances may be associated with the device, not only by being carried within their interiors, but also by application of a coating to the device. Alternatively, the substance may be dispersed in the composition of the device material. Alternatively, the implant may be fabricated entirely of the angiogenic substance. Recognizing that there are many ways to attach an angiogenic substance or drug to a device, the methods listed above are provided merely as examples and are not intended to limit the scope of the invention. Regardless of the method of association, the implants of the present invention interact with the surrounding blood and tissue to distribute the angiogenic substance into the ischemic tissue.

Additionally, each implant embodiment serves to provide a constant source of irritation and injury to the tissue in which it is implanted, thereby initiating the healing process in that tissue that is believed to load to angiogenesis. As tissue surrounding the implant moves, such as the contraction and relaxation of muscle tissue, some friction and abrasion from the implant occurs, which injures the tissue. The injury caused by the outside surfaces of the implants to the surrounding tissue does not substantially destroy the tissue, but is sufficient to instigate an injury response and healing which leads to angiogenesis.

Structurally, the implant devices may be configured in a variety of shapes to carry out the objectives outlined above for initiating angiogenesis. Additionally, varying degrees of flexibility are acceptable for carrying out the implant function. By way of example, the implant device may comprise a capsule or tubular shaped device formed from a flexible material such as a polymer or superelastic metal alloy and having at least one opening to the device interior to permit blood to enter and exit.

One or more implants of the present invention may be applied to an area of ischemic tissue. By way of example, the implants may define a width of approximately 2 mm and a length corresponding to somewhat less than the thickness of the tissue into which it is implanted. It is anticipated that implants having a 2 mm wide profile would serve an area of ischemic tissue of approximately one square centimeter to adequately promote angiogenesis throughout the surrounding region of tissue yet avoid altering the movement of the tissue due to a high density of foreign objects within a small region.

The devices may be delivered to the intended tissue location percutaneously and transluminally, thoracically or surgically by a cut down method. In the case of implants placed within myocardial tissue of the heart, delivery systems are disclosed for percutaneously accessing the left ventricle of the heart and penetrating and delivering the implant into the myocardium.

It is an object of the present invention to provide a method of promoting angiogenesis within ischemic tissue.

It is another object of the present invention to provide a method of promoting angiogenesis by implanting a device within ischemic tissue.

It is another object of the present invention to provide a process of promoting angiogenesis within ischemic myocardial tissue of the heart.

It is another object of the invention to provide an implant suitable for implantation within tissue of the human body.

It is another objective of the present invention to provide an implant delivery system that is safe and simple to use while minimizing trauma to the patient.

It is another object of the invention to provide an implant that will irritate tissue that surrounds the implant to initiate a healing response that leads to angiogenesis.

It is another object of the invention to provide an implant that is configured to have associated with it an angiogenic substance that promotes angiogenesis within tissue surrounding the implant.

It is another object of the invention to provide an implant configured to interact with blood present in the tissue into which the implant is inserted.

It is another object of the invention to provide an implant that defines an interior into which blood can enter and thrombose.

It is another object of the invention to provide an implant to which a thrombus of blood or an angiogenic substance can be inserted before or after the implant has been inserted into tissue.

BRIEF DESCRIPTION OF THE DRAWINGS

The foregoing and other objects and advantages of the invention will be appreciated more fully from the following further description thereof, with reference to the accompanying diagrammatic drawings wherein:

FIG. 3A is a cut-away illustration of a percutaneous delivery device delivering an implant configured as a capsule to a tissue location;

FIG. 3B is a partial cut-away view of a delivery device penetrating the tissue location and delivering an implant configured as a capsule;

DESCRIPTION OF THE ILLUSTRATIVE EMBODIMENTS

Figure 1A:
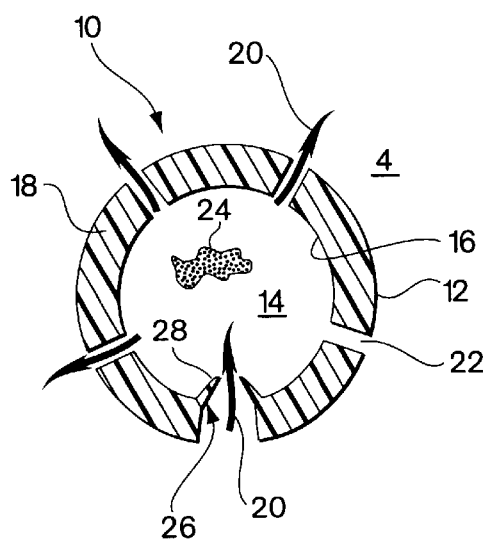
FIG. 1A is a sectional illustration of the flexible implant configured as a capsule and having a check valve.
Figure 1B:
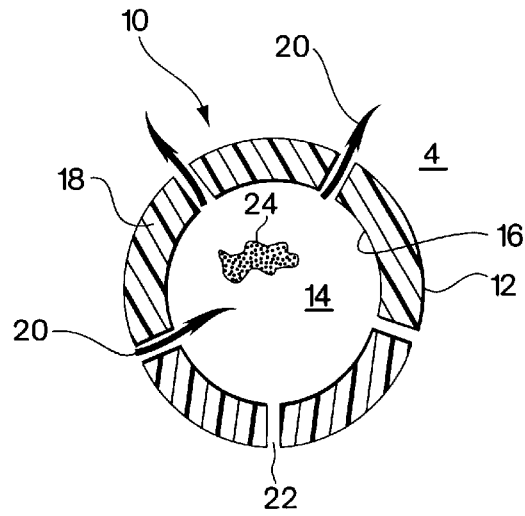
FIG. 1B is a cross-sectional diagram of the flexible implant configured as a capsule.

FIGS. 1A and 1B show one embodiment of the implant device comprising a capsule 10. The capsule embodiment has an exterior surface 12, a volume defining interior 14 with an inside surface 16. The wall 18 of the capsule may be somewhat flexible to permit flexure with the movement and compressive forces of the surrounding tissue 4 into which it is implanted. However, the wall should be fabricated to provide sufficient structural support to resist complete collapse of the capsule when it flexes.

Blood flow, represented by arrows 20, is intended to enter and exit the implant as part of the function of the device. As shown in FIG. 1B, blood 20 from the surrounding tissue 4 enters the interior 14 of the implant 10 through an opening 22. There may be several additional openings 22 to increase the amount of blood that an be exchanged through the device. Movement of the surrounding myocardial issue 4 with the pumping of the heart flexes the capsule 10 and promotes blood interchange with the interior 14. When implanted in muscle tissue, such as myocardial tissue of the heart, contraction of the muscle tissue compresses the capsule 10, reducing the volume of interior 14, causing blood to be ejected through openings 22. Relaxing of the surrounding muscle relieves pressure on the capsule, permitting it to expand resiliently back to a non-compressed configuration in which the interior volume is maximized and ready to receive blood flow. The cyclical pumping of the heart and associated expansion and contraction of the myocardium provide a mechanism for exchanging blood through the capsule 10. Additionally, the capsule may be provided with an opening having a check valve 26 as shown in FIG. 1A. The check valve can be formed in the wall 18 of the capsule by forming at least one flap 28 that opens inwardly under fluid pressure from the exterior but does not open outwardly from the pressure of fluid within the interior 14. The check valve allows blood flow into the interior of the capsule but prevents flow back out of the valve to provide additional flow control.

While in the interior 14 of the implant, the trapped blood pools and tends to coagulate. The coagulated blood forms a thrombus that is believed to provide a mechanism for triggering angiogenesis. As the bolus of blood thromboses, fibrin and arterioles are formed. New blood vessels emerge in the new tissue growth to provide blood flow to the ischemic region. The new blood vessels, not only serve the site of new tissue formed by fibrin growth induced by the presence of the implant, but will also extend to surrounding areas of the myocardium.

Alternatively or in addition to relying on pooling of blood in and around the implant, a thrombus of blood, previously removed from the patient's body may be inserted into the interior of the implant prior to implantation to help initiate the process of angiogenesis. The thrombus may be loaded into the capsule through a hypodermic needle and syringe inserted through an opening 20. The pre-loaded thrombus of blood permits the implant to initiate the angiogenesis process at a more advanced stage.

Alternatively or in addition to providing a thrombus of blood in the interior 14 of the implant, the blood may contact and mix with an angiogenic substance 24 previously placed in the interior 14 of the device. The angiogenic substance may be applied to a thrombus that is preloaded into the interior of the implant or may be loaded independently into the interior. The angiogenic substance may be delivered into the capsule with a hypodermic needle and syringe through an opening 20. In the case of a solid angiogenic substance, blood flow 20 entering the interior 14 would gradually erode the substance and carry it to the surrounding myocardial tissue 4 as part of the interchange of the blood with the device to provide a time released effect. The angiogenic substance may also be a fluid to mix more readily with bloodflow and also to leech directly from the implant through openings 22. The angiogenic substance continuously mixes with and is carried by the blood into the surrounding myocardial tissue 4 in a controlled quantity dictated by the size of the implant openings 22 and the viscosity of the substance 24. By altering the opening 22 size and fluid substance viscosity, the flow rate of the substance into the surrounding tissue can be tailored. Angiogenic substances also may be associated with the implant either by coating the surfaces of the implant or by intermingling molecules of the substance through the pores of a porous material that is used to form the wall of the implant or of a porous material that is adhered to the surface of the implant.

As mentioned above the tissue healing process, including thrombosis and fibrin growth, is believed to induce the growth of new blood vessels in the healing tissue which extend through surrounding tissue. The implants of the present invention may be configured to further trigger a healing response in surrounding myocardial tissue 4 by having an outer surface 12 that is configured to irritate the tissue as it contacts the surface. The surface 12 may be roughened, characterized by small projections that abrade the surrounding myocardial tissue as it continuously moves against the surface of the implant. Thus the implant provides a mechanism for triggering ongoing injury and healing of the myocardium that ultimately leads to new blood vessel growth to supply blood to the injured areas.

The capsule 10 may be any shape capable of defining a chamber or interior. The example shown in FIGS. 1A and 1B are depicted as somewhat spherical shell; however, this shape is intended merely to be illustrative of the inventive concept and is not intended to limit the scope of the invention to an implant having any particular shape. The capsule 10 may be formed from any material having the requisite strength, when configured in the chosen shape, to resist substantial compression by contracting tissue 4 that will surround the implant. The implant may be formed from a stainless steel or from a polymer and may be made to be bioabsorbable. In a preferred embodiment, the capsule is formed from a high density polymer and is formed by a molding process suitable of making hollow vessels such as blow molding or spin molding. Alternatively the capsule may molded in two halves that are later fused together. Openings 22 may be formed after the capsule is formed by piercing, punching, drilling or laser energy.

Figure 2A:
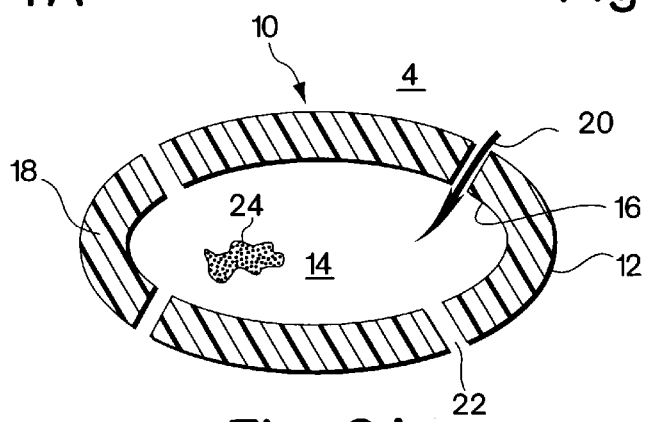
FIG. 2A is a cross-sectional figure of a highly flexible implant configured as a capsule.
Figure 2B:
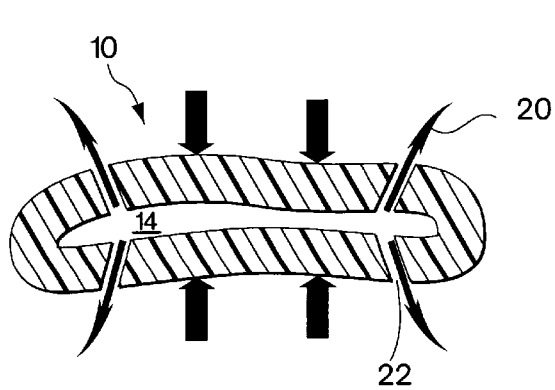
FIG. 2B is a cross-sectional diagram of a highly flexible implant configured as a capsule in a compressed configuration.
Figure 2C:
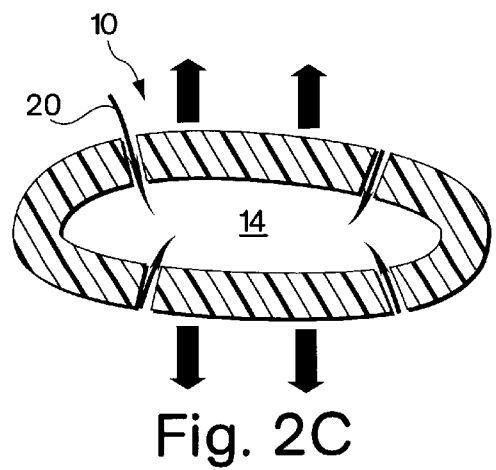
FIG. 2C is a cross-sectional figure of a highly flexible implant configured as a capsule in an uncompressed configuration.

In another embodiment shown in FIGS. 2A–2C, the capsule 10 may be configured to be highly flexible so that it is easily fully compressed by the surrounding myocardial tissue 4 during periods of contraction. As the myocardial tissue relaxes, the capsule 10 returns to its uncompressed, volume defining configuration. The device shown in FIGS. 2A–2C also has at least one opening 22 to permit blood flow into and from the interior of the capsule 14 permitting blood flow 20 to freely enter the interior 14 of the capsule from surrounding myocardial tissue 4. FIG. 2A represents the capsule in its unstressed, uncompressed state. FIG. 2B represents the capsule in a collapsed state under the compressive forces of the surrounding myocardial tissue 4 in contraction, the collapsing volume forcing blood flow out of the interior 14 of the capsule. FIG. 2C represents the capsule once again returning to an uncompressed configuration when the surrounding myocardial tissue 4 relaxes during the cardiac cycle. The capsule repeatedly collapses and expands coinciding with the contraction and relaxing of the myocardial tissue 4. The flexible capsule does not resist the external forces applied by the surrounding myocardium. The capsule collapses completely upon itself and expands again to define a maximum volume with an interior 14 that is filled with blood flow 20. The large volume change repeatedly experienced when the capsule expands and compresses provides a pumping action to move the blood into and from the capsule.

As with the less flexible capsule embodiment described above, the flexible capsule uses blood flow into the interior 14 to initiate mechanisms for angiogenesis. Blood flow 20 entering the capsule 10 through openings 22 while the capsule is in its uncompressed form has an opportunity to thrombose, a process which is believed to lead to angiogenesis as discussed above. The flexible capsule 10 may be preloaded with a thrombus of blood previously obtained from the patient or with an angiogenic substance 24, which can leach out from the implant to promote angiogenesis in surrounding tissue. The greater volume change provided by the flexible capsule implant between its compressed configuration and uncompressed configuration, provides substantial pumping action, making this embodiment particularly well suited for pumping a preloaded angiogenic substance into the surrounding tissue. As discussed above in connection with the less flexible capsule embodiment, a fluid angiogenic substance may be disposed within the interior 14 of the capsule and pumped out after implantation by the motion of the capsule and flow of blood through the interior causing the substance to exit the openings 22 of the capsule. Substance viscosity and opening size may be tailored to provide a specified release rate of the substance into the surrounding tissue.

As mentioned above, several of the implant devices may be placed within an area of ischemic tissue to promote angiogenesis over a broad area that is ischemic. In the case of ischemic myocardial tissue, multiple implants should be spaced sufficiently so that the aggregate effect of the presence of foreign bodies within the tissue does not adversely alter the muscle's flexibility and function. Implants on the order of 2 mm in diameter are believed to serve an ischemic area of about 1 square cm adequately without having an adverse effect on muscular function.

Although the depth level of the implants within the myocardium is not crucial, it is believed that placing the implants closer to the endocardial surface 6 will yield the best results. The rationale for this theory is based on observations that the myocardial muscle closer to the endocardial surface appears more active in creating the pumping movement along the myocardial layer than does the myocardial area closer to the epicardium. Placing the implants in an area higher muscle activity is believed to lead to a more pronounced angiogenic response to the presence of the implants. Though it is acceptable, it is not essential that a portion of the implant be exposed to the left ventricle. The entire implant may be submerged within the myocardium, interacting with the blood that is present within the tissue. For a myocardium having a thickness of 10 mm, implants having a length on the order of 5–8 mm should be suitable to carry out the objects of the invention.

Figure 4:
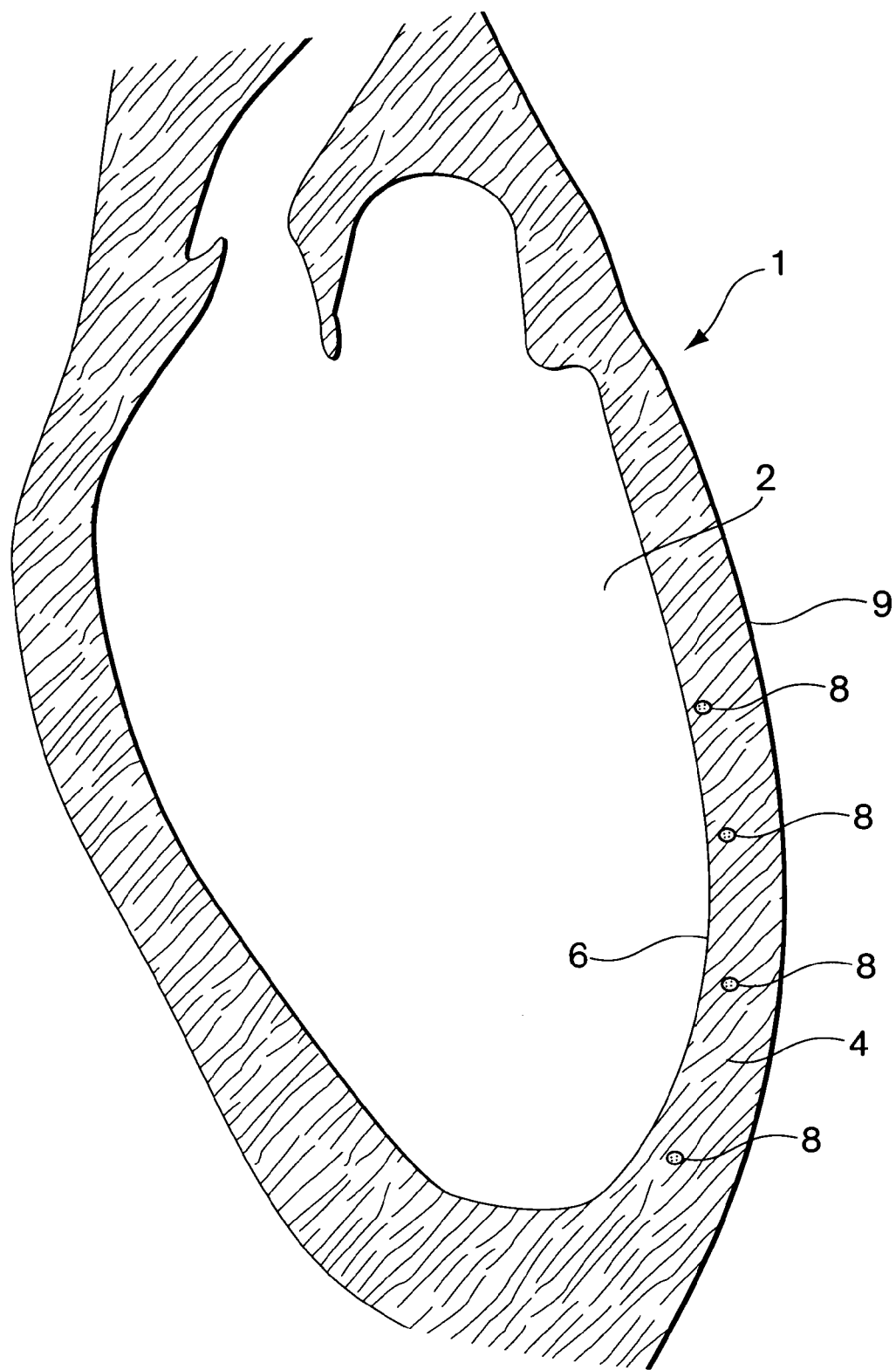
FIG. 4 is a sectional illustration of the left ventricle of a human heart having several implants placed within the myocardium.
Figure 5A:
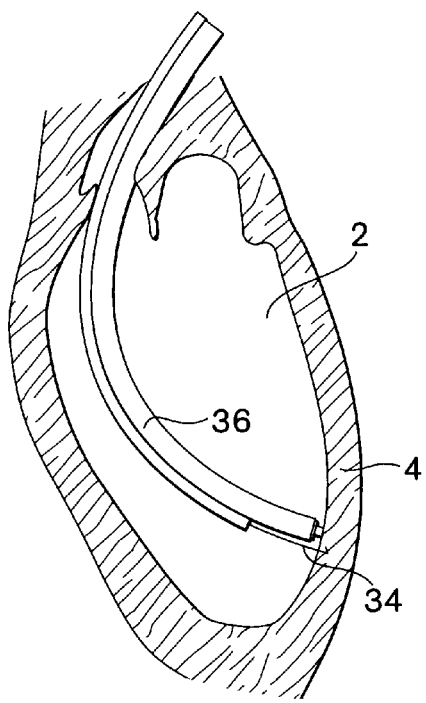
FIGS. 5A–5D illustrate the steps of percutaneously delivering several implants to an area of ischemic myocardial tissue in the left ventricle.
Figure 5B:
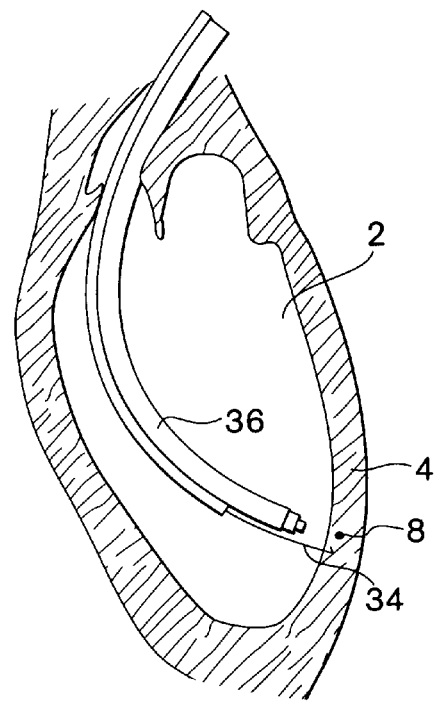
Figure 5C:
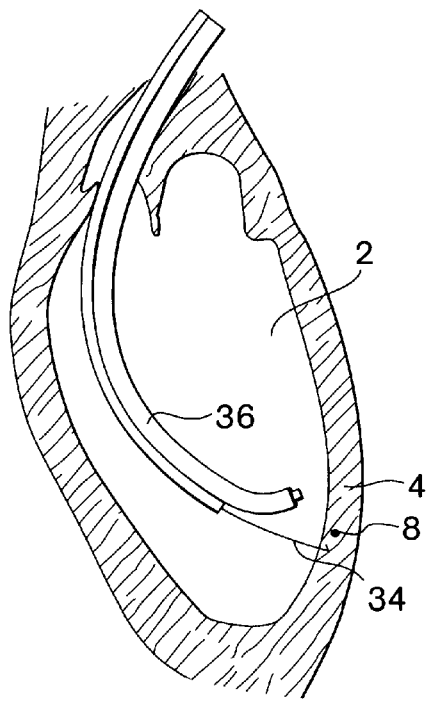
Figure 5D:
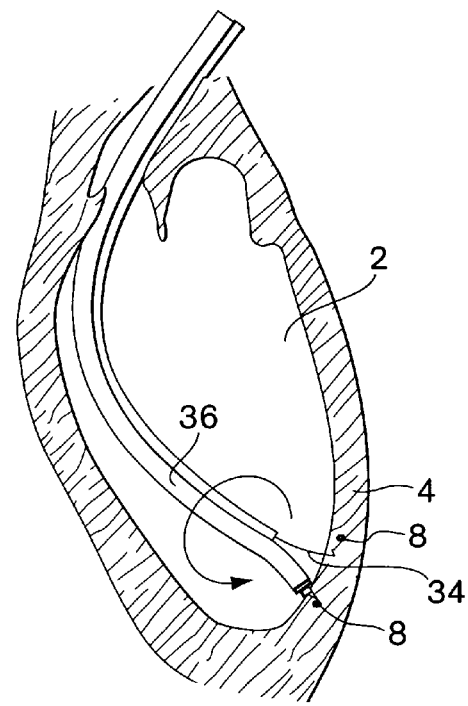

Access to ischemic tissue sites within a patient to deliver an implant may be accomplished percutaneously, surgically by a cut-down method or thoracically . However, the less invasive and traumatic percutaneous approach of delivering the implants is generally preferred. A percutaneous delivery device for delivering the capsule embodiments to the myocardium of the heart is shown in FIGS. 3A and 3B. FIG. 4 shows a diagrammatically sectional view of a left ventricle 2 of a human heart 1. Each of the implant embodiments described herein may be delivered percutaneously through a delivery catheter 36, shown in FIGS. 5A–5D, as will be described in detail below. It is noted that, throughout the description of the implant embodiments and their associated delivery systems, "proximal" refers to the direction along the delivery path leading external of the patient and "distal" refers to the direction leading internal to the patient.

To access the left ventricle of the heart percutaneously, a guide catheter (not shown) is first navigated through the patient's vessels to reach the left ventricle 2 of the heart 1. A barb tipped guidewire 34 may then be inserted through the guide catheter and into the ventricle where it pierces the myocardium 4 and becomes anchored within the tissue. After anchoring the guidewire, a steerable delivery catheter 36 may be advanced over the guidewire to become positioned within the ventricle for delivery of the implants. To facilitate delivery of multiple implants, the guidewire lumen of the delivery catheter 36 may be eccentrically located on the catheter 36. Therefore, when the catheter is rotated about the guidewire, the center of the catheter will rotate through a circular path as demonstrated in FIGS. 5C and 5D, to encompass a broader delivery area with one guidewire placement. The outside diameter of the delivery catheter is preferably less than 0.100 inch. Additionally, the delivery catheter may be provided with steering capability by means of a pull wire extending the length of the catheter and attached at its distal end such that pulling on the wire from the proximal end causes the distal tip of the catheter to be deflected. Therefore, the steering capability provides a broader range of delivery area with a single catheterization. A detailed description of the construction of a delivery catheter for reaching multiple sites within the left ventricle is described in U.S. patent application Ser. No. 09/073,118 filed May 5, 1998, the entire disclosure of which is herein incorporated by reference.

A capsule delivery catheter 40 suitable for percutaneously delivering the capsule implants 10 into the myocardium is shown in FIG. 3A. First, the steerable delivery catheter 36 is navigated into the left ventricle 2 as shown in FIGS. 5A–5D (which represent a delivery catheter 36 of a general type accessing the left ventricle 2, applicable to all implant and delivery embodiments herein described). The capsule delivery catheter 40 is inserted through the steerable delivery catheter 36. The capsule delivery catheter 40 shown in FIGS. 3A and 3B slidably receives an inner push tube 44 with a capsule carrier 42 at its distal end. The inner push tube is slidable within the catheter tube 40 and is withdrawn inside the outer tube during delivery to the myocardial site throughout the steerable catheter. After reaching the myocardial site, the inner push tube is moved distally with respect to the catheter tube 40 to extend the capsule carrier past the distal tip of the catheter prior to advancement into the tissue.

The capsule carrier 42 is shaped to have a concave cradle 50 suitable for pushing the capsule 10 through the lumen 41 of the capsule catheter during delivery. Extending distally past the cradle 50 on the capsule carrier in a piercing distal tip 48 that pierces the endocardium 6 at the selected site as the inner push tube 44 is moved distally. As shown in FIG. 3B, continued distal movement of the push tube 44 causes the capsule carrier to penetrate the myocardium through the penetration site initiated by the piercing tip 48. Only the endocardial surface presents any measurable resistance to penetration, and once it is penetrated by the piercing tip 48, continued penetration into the myocardium 4 presents little additional resistance. Therefore, the capsule carrier 42 with a capsule 10 nested within the cradle 50 can penetrate into the myocardium 4 with little resistance or interference with the capsule 10. Once the cradle portion 50 of the capsule carrier 42 has penetrated the endocardial surface, a push wire 52, slidable within the push tube 44 and capsule carrier 42, is moved distally through cradle port 51 to push the capsule 10 from the cradle area 50 so that it becomes implanted within the myocardium 40. After implantation, the push wire 52 and push tube 44 with capsule carrier 42 are withdrawn proximally into the catheter tube 40 so that the steerable delivery catheter 36 may be withdrawn from the ventricle. The piercing tip 48 of the capsule carrier 42 should be sheathed within the catheter tube 40 during entry and withdrawal so as not to inadvertently pierce other areas of tissue.

The catheters and push tube described above may be fabricated from conventional materials known in the art of catheter manufacture. The push wire 52 also may be fabricated from conventional materials known in the guidewire art: stainless steel or a plastic material. The capsule carrier 42 may be fabricated from a rigid polymer or stainless steel and joined to the distal end of the push tube 44 by any conventional means of bonding. The cradle area 50 should be configured to nest and hold the capsule during delivery to permit passage of the push wire 52 through cradle port 51 so that the capsule can be pushed from the cradle into the myocardium. By way of example, the cradle 50 may have a concave, dish-like shape if intended to hold a spherical shaped capsule as has been described.

Figure 6A:
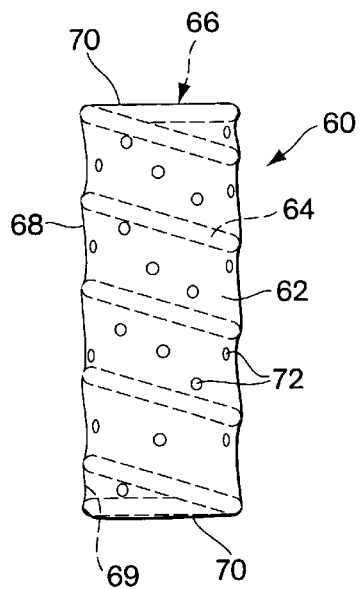
FIG. 6A is a side view of a flexible implant configured as a flexible tube.
Figure 6B:
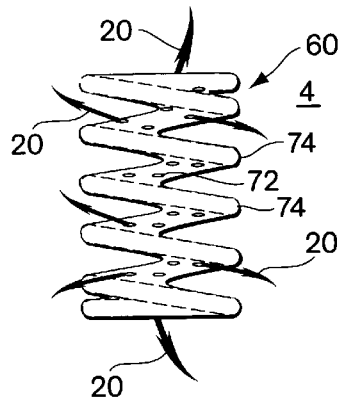
FIG. 6B is a side view of the flexible tube implant compressed by the tissue that surrounds it.
Figure 6C:
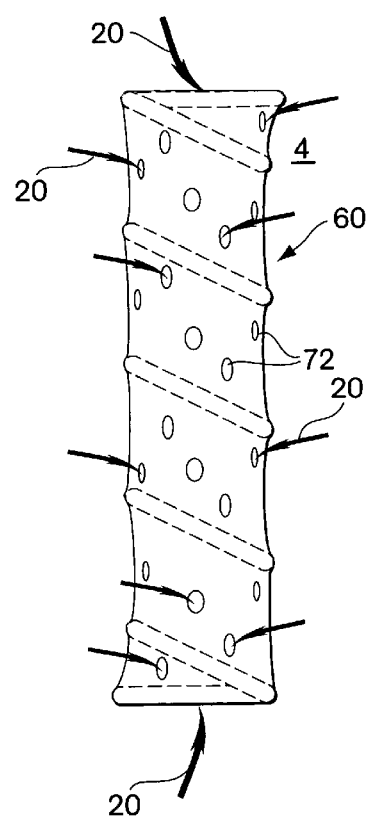
FIG. 6C is a side view of the flexible tube implant in an uncompressed, expanded configuration.

Another flexible implant embodiment is shown in FIGS. 6A–6C. A flexible tube 60 is provided that is configured for significant longitudinal compression and expansion as shown in FIGS. 6B and 6C under the force of the cyclical contraction and relaxation of muscle tissue into which it is implanted, such as that of the myocardium. As with the flexible capsule embodiment discussed above, the flexible tube embodiment 60 initiates angiogenesis in part by its interaction with blood flow into and from the device as well as its dynamic movement within the myocardial tissue while implanted. The tube embodiment 60 is comprised of a flexible sleeve 62 of a thin flexible polymer material such as polyimide. The sleeve defines an interior 66 and has an outer surface 68 and inner surface 69. A flexible coil spring 64 shown in phantom in FIG. 6A may reside within the interior 66 against the inner surface 69 to support the sleeve 62 in an open, tubular configuration. While providing radial support, the also coil permits longitudinal compression of the sleeve shown in FIG. 6B and helps to provide resilience to the sleeve so that it may recover to an elongated tubular shape when the surrounding tissue relaxes as is shown in FIG. 6C.

When the surrounding tissue is in a relaxed state, the flexible tube 60 maintains an uncompressed tubular shape that permits blood to enter the interior 66 through end openings 70 and side openings 72 of the sleeve 62. Blood within the interior 66 of the flexible tube 60 will tend to thrombose which leads to angiogenesis as described above in connection with the capsule embodiments. Additionally, as with the capsule embodiments, a thrombus of blood and/or angiogenic substance may be loaded into the flexible tube implant 60 to interact with blood flow 20 to further enhance the process of angiogenesis. Substances may be placed within the interior 66 of the tube 60 prior to implantation or after the tube has been implanted into the myocardium by inserting the substance through an opening 70. Alternatively, a coating containing an angiogenic substance may be applied onto the sleeve 62 or a substance may be embedded within the structure of the sleeve material. Compression of the flexible tube as shown in FIG. 6B causes blood flow 20 along with angiogenic substances to be ejected outward through opening 70 and 72 into the surrounding tissue 4.

As mentioned above in connection with the capsule embodiment, movement of the implant in the myocardium during the cardiac cycle also tends to initiate angiogenesis by irritating or slightly injuring the tissue. The flexible tube 60 forms a plurality of pleats 74 when it is compressed longitudinally as shown in FIG. 6B. As the tube 60 flexes during the cardiac cycle, the cyclical formation of pleats 74 created by the collapse of sleeve 62 project outward into surrounding tissue 4 when the muscle tissue is in contraction. As the muscle tissue 4 relaxes, the tube returns to its uncompressed form drawing up slack in the sleeve 62 to withdraw pleats 74. The repeated formation and retraction of each pleat will irritate a small area of surrounding tissue. The plurality of pleats, therefore, provide a plurality of nucleation sites where angiogenesis can be initiated with a single implant.

Figure 7A:
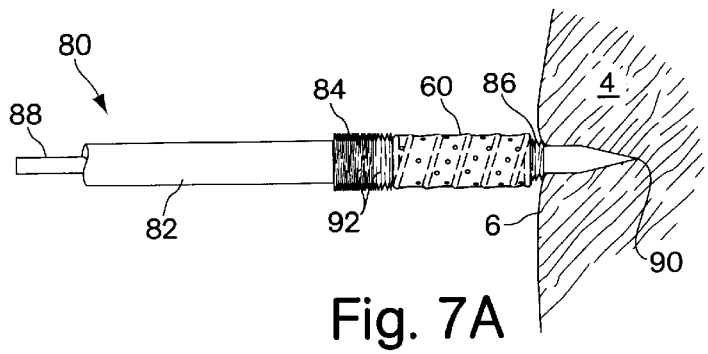
FIG. 7A is a side view illustration of the flexible tube implant being delivered to an intended tissue location on a delivery system.
Figure 7B:
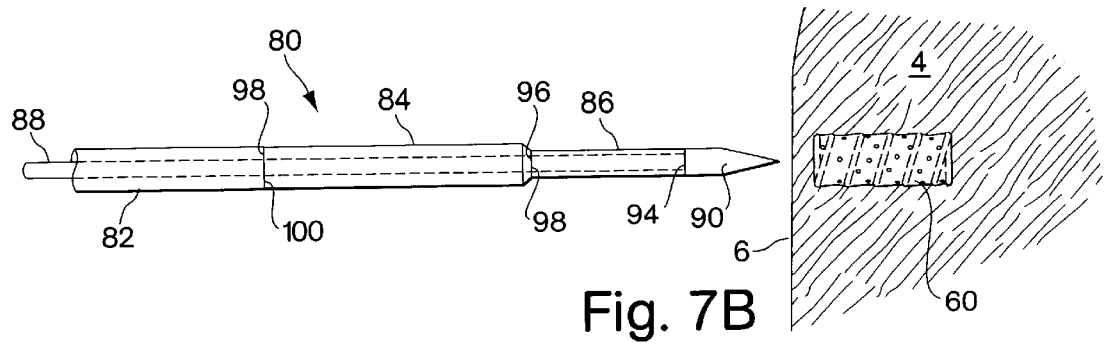
FIG. 7B is a side view of a delivered implant within tissue and the withdrawing delivery device.

A percutaneous delivery device for implanting the flexible tube into myocardial tissue of the heart is shown in FIGS. 7A and 7B. The delivery device 80 is comprised of a catheter that is percutaneously deliverable to the heart through a guide catheter and a steerable catheter 36 that is advanceable to the intended myocardial implant location through the left ventricle as shown in FIGS. 5A–5D. Within the steerable delivery catheter 36 is slidable, the flexible tube implant delivery system 80 shown in FIGS. 7A and 7B. The delivery device catheter 80 has a tubular push shaft 82 having joined at its distal end a proximal crinkle tube 84, which is joined at its distal end to a distal crinkle tube 86 of a smaller diameter than the proximal crinkle tube 84. Slidable within the push tube 82 is a piercing wire 88 having a sharpened distal tip 90 that is suitable for piercing the endocardium 6 to implant the device. The distal crinkle tube 86 is attached at its distal end to the distal end of the push wire 88. The crinkle tubes are formed from a thin flexible material that will collapse into a random pattern of pleated folds when placed under an axial compressive load. A suitable material for the crinkle tubes is polyethylene or polyethylene terephthalate. As the crinkle tubes collapse, the pleats of the wall serve to increase the overall profile of the tube. When collapsed within the tubular implant 60, the pleats 92 of the crinkle tubes contact the inside surface 69 of the tube to hold it during delivery into the myocardium.

The proximal crinkle tube 84, having a larger diameter than the distal crinkle tube presents a larger profile when collapsed into pleated form. The larger diameter crinkle tube is intended to collapse to a profile that is larger than the diameter of the tubular implant 60 so that during delivery the crinkle tube will butt against the proximal end of the tubular implant to provide a pushing force as it is inserted into the myocardial tissue 4.

The crinkle tubes are compressed and expanded by moving the push wire 88 longitudinally with respect to the push tube 82. The distal end of the distal crinkle tube 86 is heat bonded to the distal end of the push wire 88. The proximal end 94 of the distal crinkle tube 86 is bonded to the distal end 90 of the push wire 88 and the proximal end 96 of the distal crinkle tube is bonded to the distal end 98 of the proximal crinkle tube 84. The proximal end 98 of the proximal crinkle tube 84 is bonded to the distal end 100 of the push tube 82. The crinkle tubes are collapsed to their larger profile by pulling the push wire 88 proximally and pushing the push tube 82 distally, drawing their distal ends together, to apply an axial compressive load upon both crinkle tubes simultaneously, collapsing them. The crinkle tubes return to their reduced profile by pulling them taut which is accomplished by moving the push wire distally and the push tube proximally.

Using the delivery system 60, a tubular implant is placed over the distal crinkle tube 86 while the tubes are in a taut low profile configuration. The push tube and pull wire are moved relative to each other to compress both crinkle tubes simultaneously causing the pleats of the distal crinkle tube 86 to engage the inside surface 69 of the tubular implant. The pleats 92 of the proximal crinkle tube 84 bunch up proximal to the tubular implant 60 and present a profile that is larger than the diameter of the tube to provide a backstop to prevent proximal movement of the implant on the delivery system during implantation into the tissue 4. The distal crinkle tube 86 also serves to hold the tubular implant 60 in place on the delivery device during implantation by virtue of the frictional engagement created between the pleats 92 of the crinkle tube and the interior surface of the implant 69. Alternatively, as is described below with regards to other implant embodiments, the delivery device may comprise a single, distal crinkle tube that engages the interior of the implant to locate the implant on the delivery catheter.

With the crinkle tubes in their compressed configuration, tubular implant secured over the distal crinkle tube, the delivery device 80 is advanced distally to the intended location on the endocardial surface 6. Both a push tube 82 and push wire 88 are advanced distally in unison to pierce the endocardium 6 with the sharp distal tip 90 of the push wire 88 as shown in FIG. 7A. Further distal advancement of the push wire 88 and push tube 82 serves to insert the tubular implant 60 into the tissue 4. As mentioned above in relation to the capsule implant embodiment, the implants may be placed anywhere within the myocardium, either embedded to some depth within the tissue or placed such that the proximal end of the implant meets the endocardial surface 6 and is open to the left ventricle 2. After the implant 60 has been placed in the myocardium, the push tube 82 is pulled proximally, while maintaining the push wire 88 in position to pull the crinkle tubes 84 and 86 taut, releasing them from the interior surface 69 of the implant. The delivery device 80 may then be withdrawn from the myocardium leaving the implant in place. After delivery of the implant, a substance, such as a thrombus of blood or angiogenic substance, may be inserted into the interior 66 of the implant. Such a substance may be delivered through a lumen of the delivery catheter 80, push tube 82 or push wire 88 (if fabricated from hypodermic tubing) into the distal open end 70 of the device. Fluid pressure applied from the proximal end of the shaft would cause the substance to be delivered and ejected through a distal opening, possibly formed in the sharpened tip 90 directly into the interior 66.

Another flexible implant embodiment which is formed from a porous material is shown in FIGS. 8A–8E. A porous implant 91 is shown in a tubular configuration, but may be any shape that is implantable in tissue. Preferably, the shape of the porous implant 91 defines an interior 93 into which blood flow 20 may enter from the surrounding tissue 4. The porous material comprising the implant 91 may be a relatively stiff foam material such as expanded polyethylene or any aerated polymer. The outside diameter of the porous implant may be on the order of 2 mm and it may be of length somewhat less than the thickness of tissue into which it is implanted.

Figures 8A, 8B, 8C:
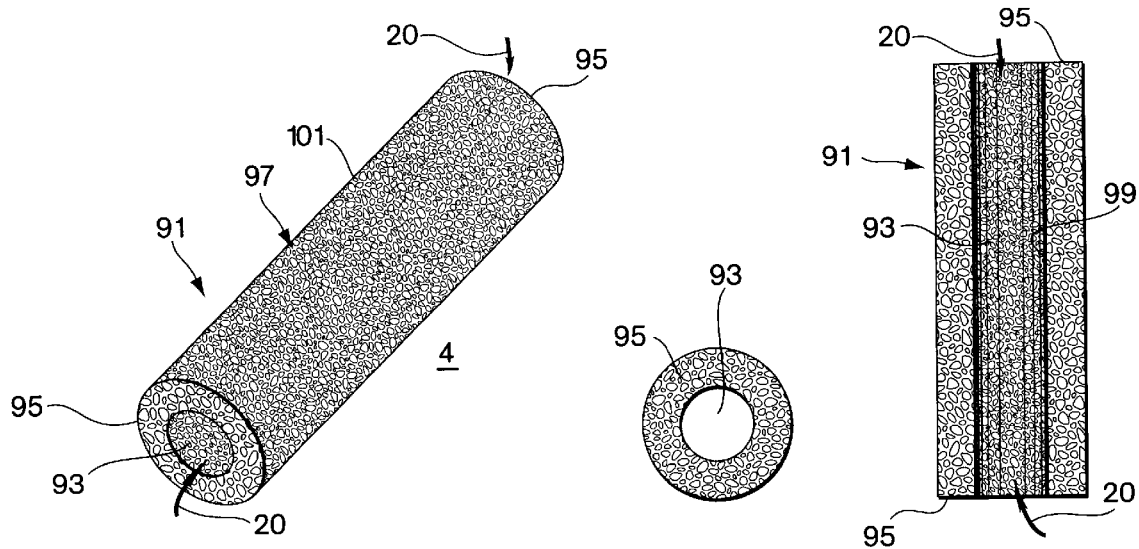
FIG. 8A is a perspective view of a porous tube flexible implant.
FIG. 8B presents a sectional view of the porous tube flexible implant.
FIG. 8C presents an end view of the porous tube flexible implant.

The porous material provides flexibility to the implant, permitting it to be compressed with contractions of the surrounding tissue and permitted to expand to an uncompressed configuration when the tissue relaxes. As with the previous embodiments, it is expected that, once implanted in the ischemic tissue blood flow 20 will enter the ends 95 of the implant while it is in its uncompressed configuration, as shown in FIG. 8B. Blood will then be forced out of the interior 93 of the implant when it is compressed by the surrounding tissue 4 in contraction. The inflow and outflow of the blood created by the cyclic compression and expansion of the flexible device encourages blood collection and thrombus formation within the interior 93 of the device which can lead to angiogenesis as described above in connection with the previous flexible implant embodiments. Additionally, the porous material 97 from which the implant is formed, such as the open cell structure of foam, will encourage blood pooling leading to fibrin and tissue ingrowth throughout the implant structure while it is implanted in the ischemic tissue 4. Each open cell 101 of the foam material provides a protective cavity into which blood flow can recede after entering the device.

Not only does the interior 93 of the implant provide a location for holding an angiogenic substance, but the entire open cell structure of the implant provides a network of small spaces defined by the open cells, which may hold a liquid or solid substance that can leach out from the implant or become mixed with blood entering the interior 93, which serves to carry the substance into the surrounding myocardial tissue 4 as blood flow 20 exits the implant. The network of open spaces defined by the foam material also provides numerous friction contact points that will irritate surrounding tissue with relative movement of the implant with respect to the tissue. It is expected that the numerous irritation points will result in numerous nucleation points where angiogenesis will begin.

Figure 8D:
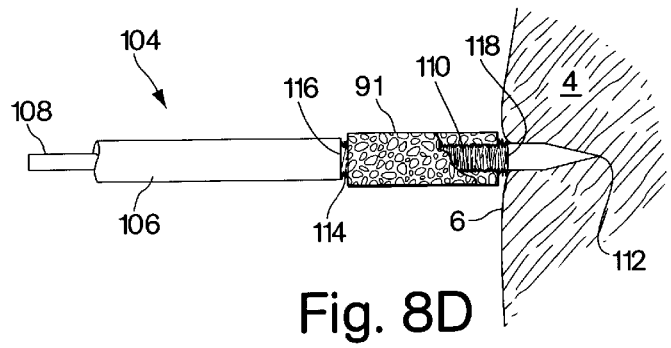
FIG. 8D is a side view of the porous tube flexible implant being delivered to an intended tissue location on a corresponding delivery system.

The porous implant 91 may be delivered to the intended tissue location by the methods described above. Specifically, as shown in FIG. 8D, the implant 91 may be delivered percutaneously, navigated to the intended location, such as the myocardium, over the distal end of a delivery catheter 104 as is shown in FIG. 8D. A generally tubular shaped porous implant may be delivered over a delivery catheter 104 comprised of a crinkle tube 110 that is configured to buckle under a compressive load, forming multiple folds 114 along its length, each of a greater diameter than the crinkle tube exhibited in a non-folded configuration. The increased diameter folds 114 engage the interior surface 99 of the porous tube to locate it on the catheter 104.

The proximal end 116 of the crinkle tube is mounted to distal end of the push tube 106 and the proximal end 118 of the crinkle tube is bonded to the piercing distal end 112 of push wire 108 that is slidable within the push tube 106. Compressive force is applied by moving the push tube 106 distally while drawing the push wire 108 proximally, bringing their distal ends together to collapse the crinkle tube 110. With the implant 91 positioned over the crinkle tube in the collapsed configuration, the folds 114 of the crinkle tube hold the implant, not only by engaging the inside surface 99 of the implant, but also by bunching and creating a stop at the proximal end 116 of the crinkle tube 110 against which the implant can rest during insertion into the myocardium 4. In this configuration, the delivery catheter 104 is moved distally so that the piercing tip 112 of the push wire 108 penetrates the endocardial surface 6 of the myocardium 4.

Figure 8E:
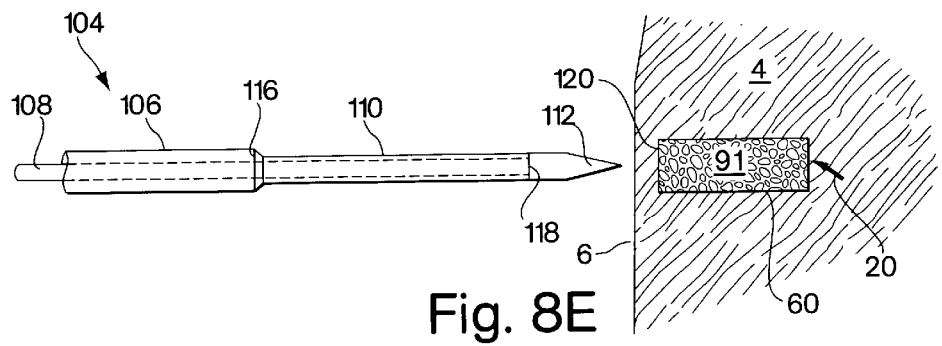
FIG. 8E is a side view of a porous flexible implant delivered into tissue and the withdrawing delivery system.

As described above, the implant may be inserted so that its proximal end 120 is flush with the endocardial surface 6 or so that the implant 91 is completely within the myocardium 4 and not open to the left ventricle as is shown in FIG. 8E. Although the implant may be placed at any depth within the myocardium, it is believed that greater muscle activity and blood flow occurs in the myocardium near the endocardial surface than occurs near the epicardial surface. Therefore, the opportunity for triggering angiogenesis with the implant appears to be increased if the implant is placed closer to the endocardial surface. After implantation, tension is applied to the crinkle tube 110 to release the implant from the delivery catheter 104. As shown in FIG. 8D when the crinkle tube 110 is in tension, folds 114 are removed and the overall diameter of the crinkle tube is reduced so as to disengage from the interior 93 of the implant 91. The crinkle tube 110 is pulled taut by moving the push wire 108 in a distal direction while moving the push tube 106 in a proximal direction. The taut crinkle tube 110 can then be withdrawn easily and the entire delivery catheter 104 is removed in a proximal direction from the implant 91 left within the myocardium 4.

Figure 9A:
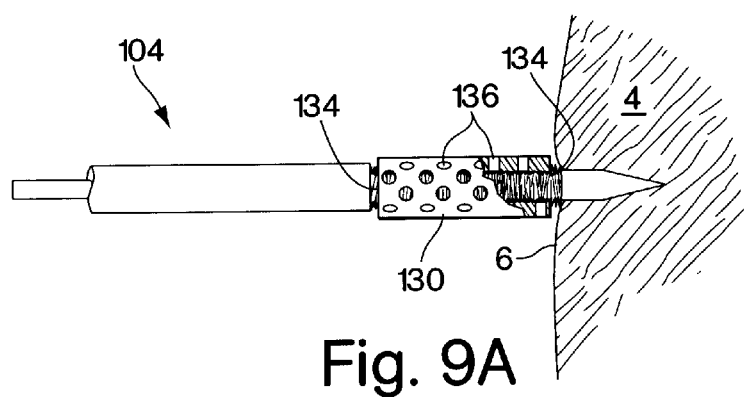
FIG. 9A is a side view of a flexible tube embodiment being delivered into an intended tissue location on its associated delivery system.
Figure 9B:
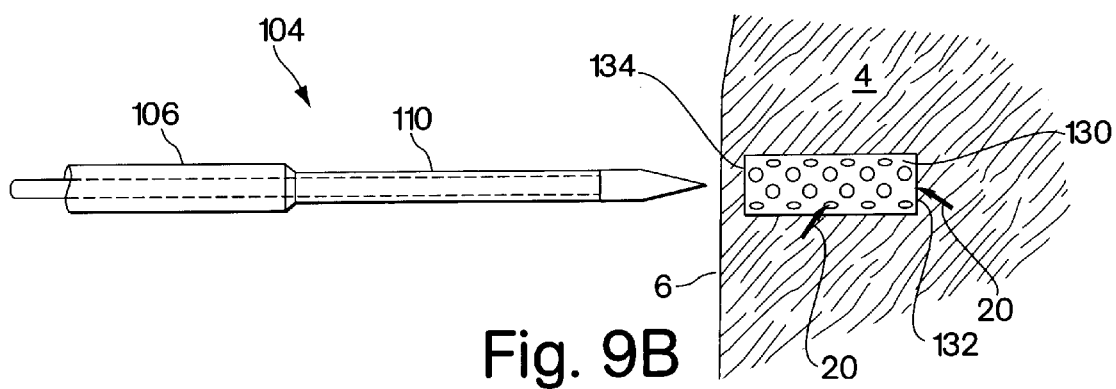
FIG. 9B is a side view of the flexible tube implant implanted within tissue and the withdrawing delivery system.

Another flexible implant embodiment is shown on its associated delivery device in FIGS. 9A and 9B. The implant 130 is intended to compress and expand to a reduced degree with the contraction and relaxation of the surrounding tissue in which it is implanted. The implant is intended to have inherent resiliency so that it returns to an open configuration under its own strength when surrounding tissue is relaxed. In this manner, the flexible tube 130 is more resilient than the flexible tube embodiment 60 described above, which requires a spring within its interior to help it return to its open configuration. The resilient tube implant 130 is similar to the capsule embodiments 10 in that it can resiliently return to a uncompressed configuration defining an interior 132. Like the capsule embodiments, the resilient implant 130 may be molded from a polymer material, such as PVC for added rigidity, or from a low density polymer to provide more flexibility when surrounding muscle tissue is contracted. In addition to end openings 134, the implant may be provided with side openings 136 to permit blood flow 20 into the implant while it is in an open configuration and out of the implant when it is compressed by surrounding muscle tissue 4. The resilient implant 130 may be formed into a tubular shape similar to the porous and flexible implants illustrated above. Configured as a tube, the implant may be delivered percutaneously to a location within the myocardium 4 by a delivery catheter 104 having a crinkle tube 110 that engages the interior of the implant during delivery as was discussed above with regards to the previous embodiment.

From the foregoing, it will be appreciated that the invention provides an implant and delivery system for promoting angiogenesis within ischemic, viable tissue. The invention is particularly advantageous in promoting angiogenesis within ischemic myocardial tissue of the heart. The implants are simple and readily insertable into the intended tissue location with a minimum of steps. The delivery systems are simple to operate to implant the devices quickly.

It should be understood, however, that the foregoing description of the invention is intended merely to be illustrative thereof and that other modifications, embodiments and equivalents may be apparent to those skilled in the art without departing from its spirit.

Having thus described the invention what we desire to claim and secure by Letters Patent is:

1. An implant device comprising a flexible body formed from a single wall, which defines an interior with a volume, the flexible body constructed to have a first configuration having a first profile and a first volume and a second configuration that is compressed to define a second profile that is different from the profile of the first configuration, and a second volume that is substantially reduced from the first volume, the implant constructed so that movement of surrounding tissue in which it is implanted causes cyclical movement of the body between the two configurations.

2. An implant device as defined in claim 1 wherein the implant has at least one opening to the interior.

3. An implant as defined in claim 2 wherein an angiogenic substance is associated with the interior of the device.

4. An implant as defined in claim 3 wherein the angiogenic substance becomes associated with the interior of the implant prior to implantation.

5. An implant as defined in claim 3 wherein the angiogenic substance becomes associated with the interior of the implant after it is implanted.

6. An implant as defined in claim 2 wherein at least one of the openings comprises a check valve configured to permit inflow of blood.

7. An implant defined in claim 2 wherein the implant is configured to permit blood inflow into the interior while in the first configuration.

8. An implant as defined in claim 7 wherein the implant is configured to permit blood to collect and thrombose within the interior.

9. An implant as defined in claim 7 wherein the implant is configured to at least partially expel contents of the interior when it moves from its first to its second configuration.

10. An implant as defined in claim 2 wherein the implant further comprises a flexible capsule.

11. An implant as defined in claim 10 wherein the capsule is generally spherical.

12. An implant as defined in claim 10 wherein the interior is completely compressed while the implant is in the second configuration.

13. An implant as defined in claim 2 wherein the implant further comprises a tube.

14. An implant as defined in claim 13 wherein the tube comprises a polymer.

15. An implant as defined in claim 14 further comprising a spring located within the interior.

16. An implant as defined in claim 14 wherein the implant further comprises a thin polymer tube that collapses to produce a plurality of folds while in the second configuration whereby the folds serve to irritate the surrounding tissue.

17. An implant as defined in claim 14 wherein the polymer is aerated to produce an open cell structure in which the open cells are configured to receive blood and permit tissue ingrowth through the structure.

18. The implant defined in claim 1 wherein an angiogenic substance to promote angiogenesis is associated with the implant.

19. An implant as defined in claim 18 wherein at least a portion of the angiogenic substance is released from the implant as it moves from the first to the second configuration.

20. An implant as defined in claim 18 wherein the angiogenic substance comprises a human growth factor.

21. An implant as defined in claim 18 wherein the angiogenic substance comprises blood.

22. An implant as defined in claim 18 wherein the angiogenic substance comprises a pharmaceutical agent.

23. An implant as defined in claim 1 wherein the implant is configured to irritate the surrounding tissue as the implant moves between its first and second configurations.

24. An implant as defined in claim 23 further comprising a plurality of surfaces to contact and irritate the surround tissue.

25. An implant for implantation in the myocardium of a patient comprising; a flexible body formed from a single wall of flexible material defining an interior and at least one opening to the interior, and the body being configured to pump blood into and out of the interior under the influence of the contraction and relaxation of the myocardial tissue into which it is implanted and the interior configured to promote thrombosis of entering blood.

26. A device for promoting angiogenesis in the myocardium comprising:

a carrier having a single wall defining a pump with a chamber implantable in the myocardium and having associated with it an angiogenic substance.

27. A device for promoting angiogenesis in the myocardium as defined in claim 26 wherein the angiogenic substance is located in the chamber.

28. A device for promoting angiogenesis in the myocardium as defined in claim 26 wherein the angiogenic substance is a thrombus of blood.

* * * * *